United States Patent [19]

VandenBerg

[11] Patent Number: Plant 7,517

[45] Date of Patent: May 7, 1991

[54] CHRYSANTHEMUM PLANT NAMED NICOLE

[75] Inventor: Cornelis P. VandenBerg, Salinas, Calif.

[73] Assignee: Yoder Brothers, Inc., Barberton, Ohio

[21] Appl. No.: 458,838

[22] Filed: Dec. 29, 1989

[51] Int. Cl.[5] ..... A01H 5/00

[52] U.S. Cl. ..... Plt./77

[58] Field of Search ..... Plt./77

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Nicole particularly characterized by its flat capitulum form; decorative capitulum type; white ray floret color; diameter across face of capitulum of from 44 to 63 mm when fully opened; short plant height with spreading and prolific branching pattern; average natural season flowering date of August 20 in Salinas, Calif. and September 24 in Hightstown, N.J.; uniform seven week photoperiodic flowering response to short days in photoperiodic controlled flowering programs; and durable, uniform performance.

3 Drawing Sheets

The present invention comprises a new and distinct cultivar of Chrysanthemum botanically known as *Dendranthema grandiflora,* and referred to by the cultivar name Nicole.

Nicole, identified as 85-033001, was originated from a cross made by the inventor Cornelis P. VandenBerg in a controlled breeding program in Salinas, Calif., in 1985.

The female parent of Nicole was the cultivar identified as Legend, a yellow flat decorative disclosed in U.S. Plant Pat. No. 6,404. The male parent of Nicole was an unnamed seedling identified as 82-M49004, a white flat decorative.

Nicole was discovered and selected as one flowering plant within the progeny of the stated cross by Cornelis P. VandenBerg in January 1986, in a controlled environment in Salinas, Calif.

The first act of asexual reproduction of Nicole was accomplished when vegetative cuttings were taken from the initial selection in April 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Nicole are firmly fixed and are retained through successive generations of asexual reproduction.

Nicole has not been observed under all possible environmental conditions. The phenotype may vary significantly with variations in environment such as temperature, light intensity and daylength.

The following observations, measurements and comparisons describe plants grown in controlled open areas in Salinas, Calif. and in Hightstown, N.J., and photoperiodic controlled programs conducted in Salinas, Calif. Rooted cuttings were established in soil and maintained outdoors under the natural temperature and daylength prevailing during June through October. Single pinching was practiced with all branches and buds retained.

The following traits have been repeatedly observed and are determined to be basic characteristics of Nicole, which, in combination, distinguish this Chrysanthemum as a new and distinct cultivar:

1. Flat capitulum form.

2. Decorative capitulum type.

3. White ray floret color, with light yellow center of capitulum.

4. Diameter across face of capitulum up to 44–63 mm when fully opened.

5. Plant height averaging 23–30 cm from soil line at time of flowering, based on a planting date of June 14 under natural daylength in Hightstown, N.J.

6. Spreading and prolific branching pattern, with an average of 7–9 branches per plant after pinch two weeks after planting a rooted cutting in Hightstown, N.J.

7. Average natural season flowering date of August 20 in Salinas, Calif., and September 24 in Hightstown, N.J., based on several years of trial flowering.

8. Uniform seven week photoperiodic flowering response to short days in photoperiodic controlled flowering programs.

9. Durable, uniform performance.

The accompanying photographic drawings show typical inflorescence and leaf characteristics of Nicole, with the colors being as nearly true as possible with illustrations of this type.

Sheet 1 is a color photograph of Nicole grown as pinched spray pot mum in a 15 cm pot.

Sheet 2 is a black and white photograph of three views of the inflorescence of Nicole.

Sheet 3 is a black and white photograph showing the upper and under sides of the leaves of Nicole at three stages of development, mature, intermediate and immature).

Of the commercial garden mum cultivars known to the inventor, the most similar in comparison to Nicole is the cultivar identified as Patriot, a white decorative disclosed in U.S. Plant Pat. No. 3,897. Reference is made to attached Chart A which compares certain characteristics of Nicole to the same characteristics of Patriot.

Similar traits are ray floret color, capitulum form and type, diameter across face of capitulum, plant height and controlled response. Nicole has a more spreading and prolific branching pattern, and a much earlier natural season flowering date than Patriot by 12 days in Salinas, Calif. and by 4 days in Hightstown, N.J.

In the following description color refrences are made to The Royal Horticultural Society Colour Chart. The clear white ray floret color of Nicole is not represented in The R.H.S. Colour Chart. The color values were determined on plant material grown in a controlled greenhouse environment in Salinas, Calif. on Sept. 19, 1989.

Classification:

*Botanical.*—*Dendranthema grandiflora* cv. Nicole.

*Commercial.*—Flat decorative spray pot mum and garden mum.

INFLORESCENCE

A. Capitulum:

*Form.*—Flat.

*Type.*—Decorative.

*Diameter across face.*—44–63 mm when fully opened.

B. Corolla of ray florets:

*Color (general tonality from a distance of three meters).*—White.

*Color (upper surface).*—White, with center of capitulum 10B for immature flowers to 10D for fully open flowers.

*Color (under surface).*—White.

*Shape.*—Flat, straight, oblong.

C. Corolla of disc florets: Not present.

D. Reproductive organs:

*Androecium.*—None.

*Gynoecium.*—Present on ray florets.

PLANT

A. General appearance:

*Heights.*—Short; 23–30 cm at time of flowering based on June 14 planting in Hightstown, N.J.

*Branching pattern.*—Spreading and prolific.

B. Foliage:

*Color (upper surface).*—147A.

*Color (under surface).*—147B.

*Shape.*—See photograph.

CHART A

COMPARISON OF NICOLE AND PATRIOT

| CHARACTERISTIC | NICOLE | PATRIOT |
|---|---|---|
| Ray Floret Color | White with light yellow center | White with light yellow center |
| Capitulum Form and Type | Flat decorative | Flat decorative |
| Branching Pattern | Spreading and prolific | Semi-upright |
| Controlled Response | 7 weeks | 7 weeks |
| Average Natural Season Flower date: | | |
| In Salinas, California: | August 20 | September 1 |
| In Hightstown, New Jersey: | September 24 | September 28 |

Comparisons Made of Plants Grown Under Natural Season Outdoor Conditions In Salinas, California and in Hightstown, New Jersey

I claim:

1. A new and distinct Chrysanthemum plant named Nicole, as described and illustrated.

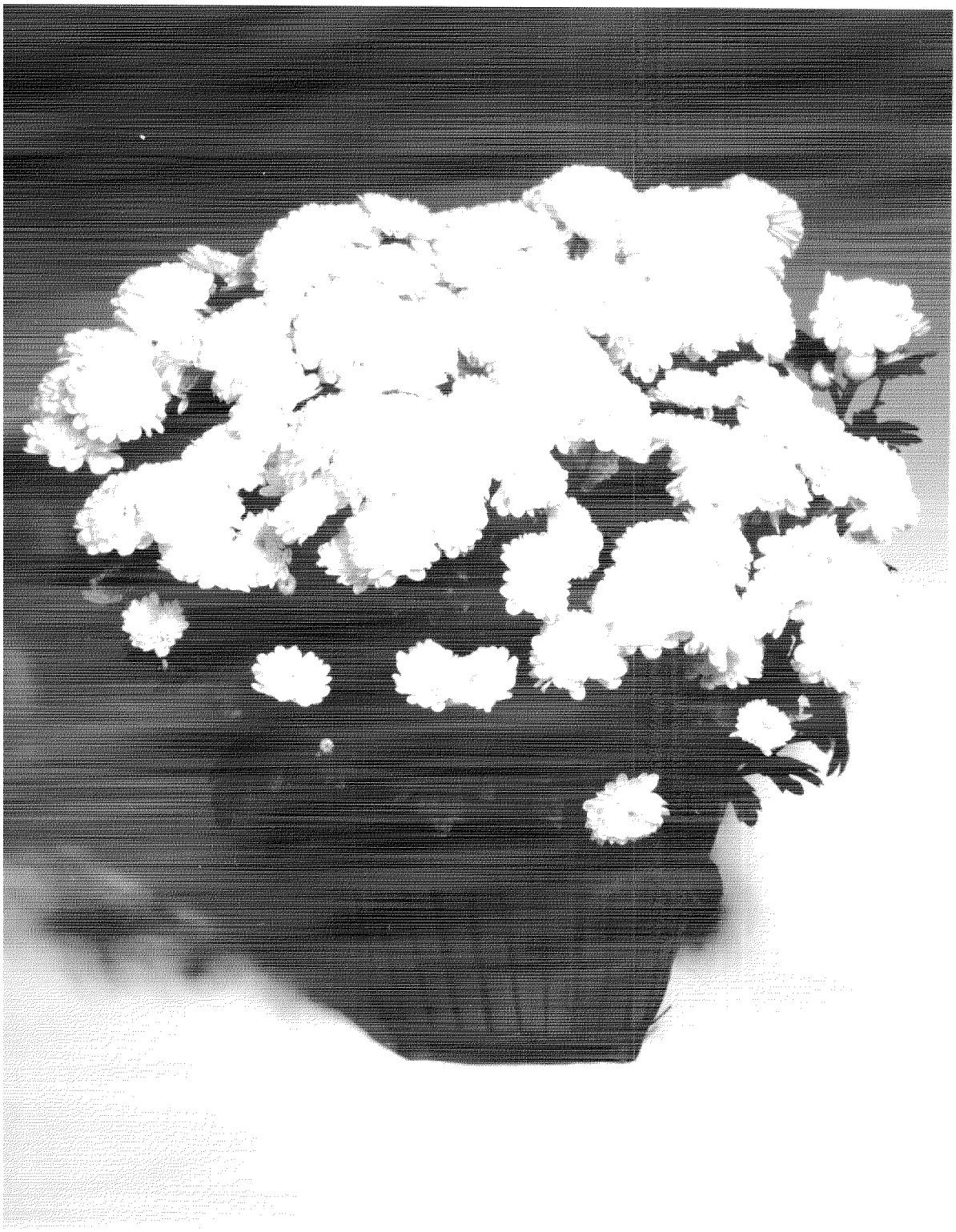

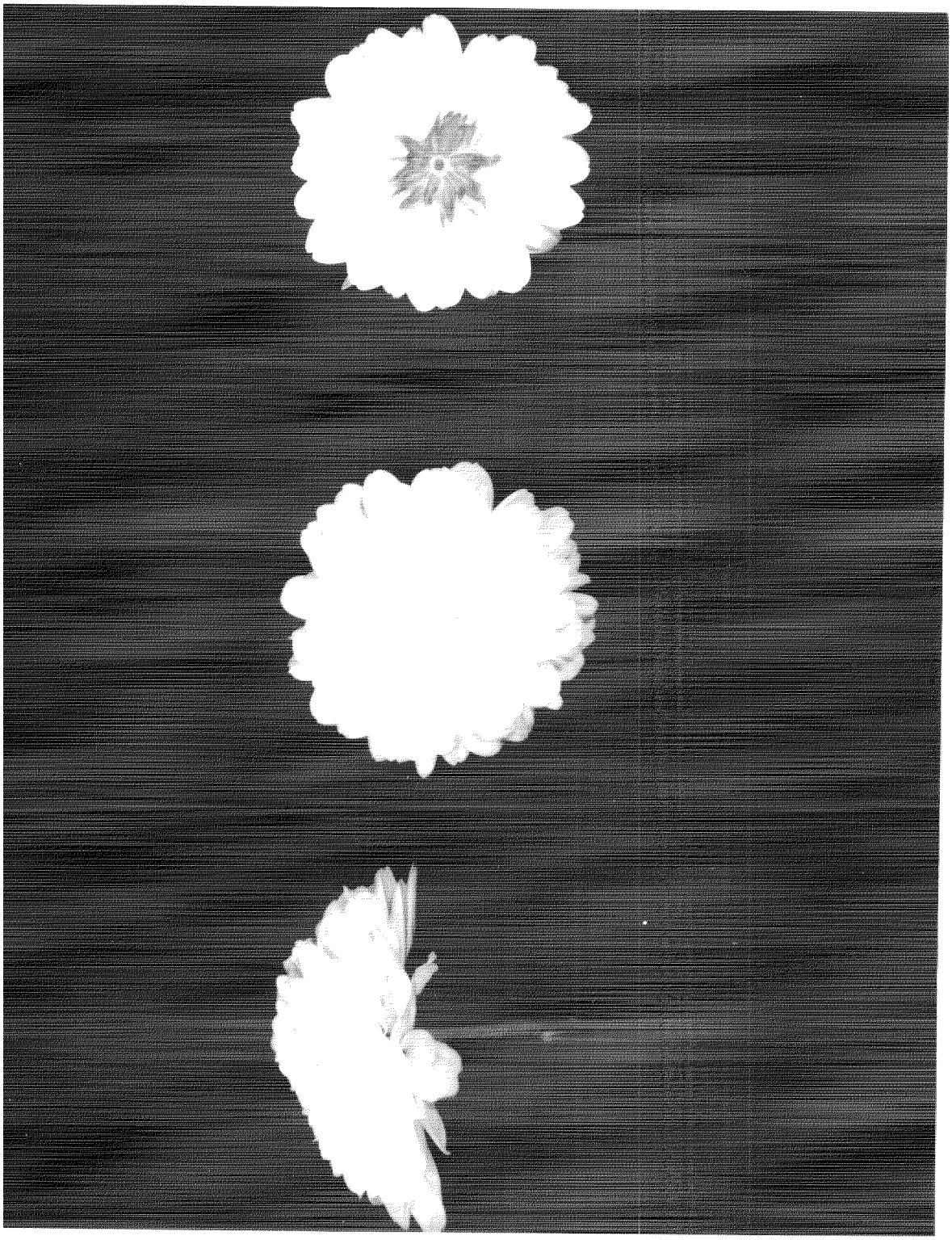

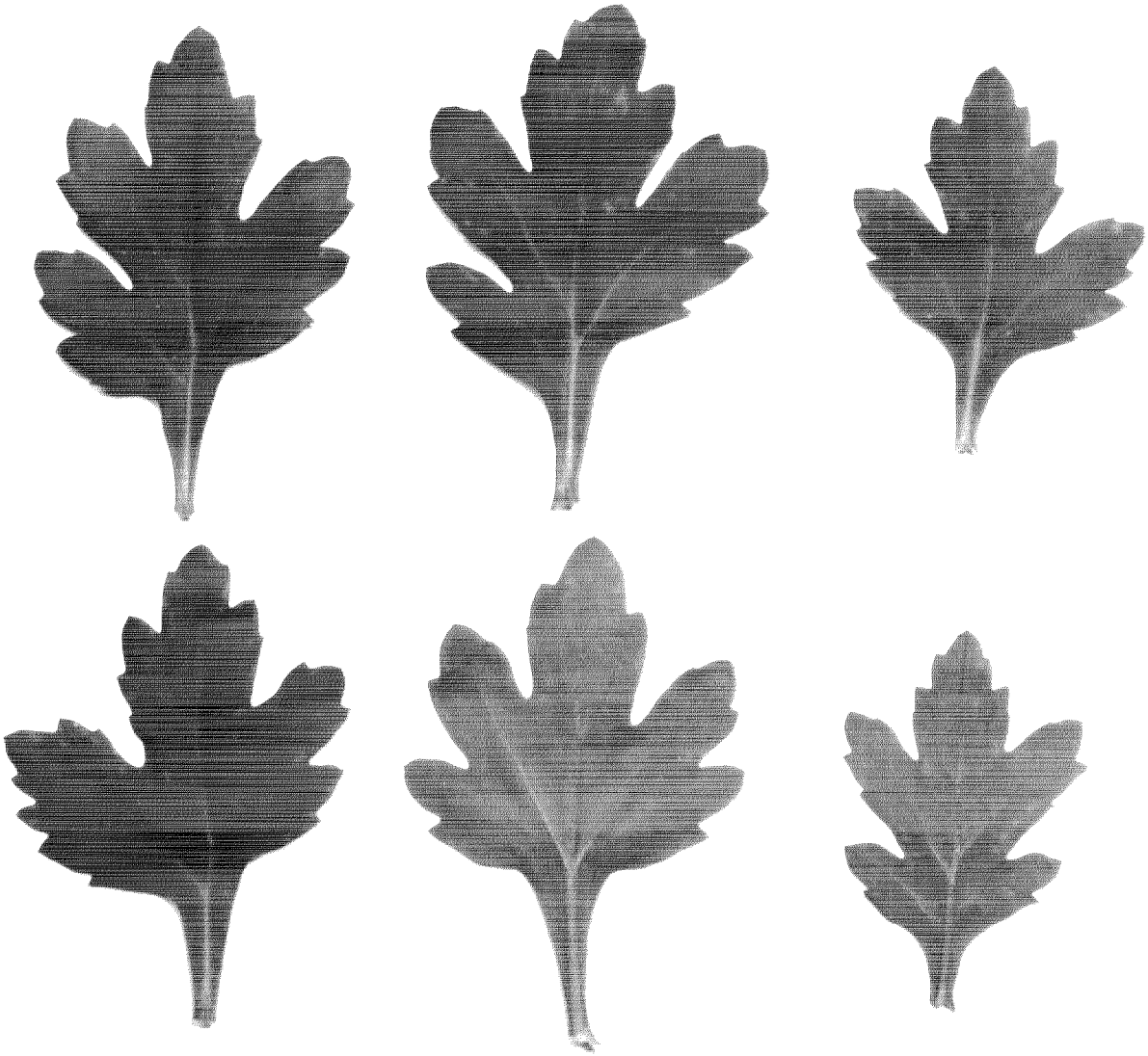

* * * * *